United States Patent [19]

Manthey

[11] Patent Number: 5,433,201
[45] Date of Patent: Jul. 18, 1995

[54] METHOD AND APPARATUS FOR STIMULATION OF POSTURE

[76] Inventor: Jürgen K. Manthey, Ebereschenstrasse 8, 0-6902 Jena, Germany

[21] Appl. No.: 54,291

[22] Filed: Apr. 30, 1993

[30] Foreign Application Priority Data

May 1, 1992 [DE] Germany .................. 42 14 523.6

[51] Int. Cl.$^6$ ............................................. A61B 8/00
[52] U.S. Cl. ................................. 128/660.02; 128/782
[58] Field of Search ................... 128/660.01, 660.021, 128/661.03, 774, 781, 782

[56] References Cited

U.S. PATENT DOCUMENTS

| | | | |
|---|---|---|---|
| 3,768,459 | 10/1975 | Cannon et al. | 128/775 |
| 4,557,275 | 12/1985 | Dempsey, Jr. | 128/782 |
| 4,665,739 | 5/1987 | Mizuno | 73/105 |
| 5,022,412 | 6/1991 | Gradovetsky et al. | 128/781 |
| 5,183,046 | 2/1993 | Beach et al. | 128/661.07 |
| 5,220,922 | 6/1993 | Borany | 128/660.01 |

FOREIGN PATENT DOCUMENTS

2496449  6/1982  France ..................... 128/661.03

OTHER PUBLICATIONS

D. Bak, "Electromagnetic Monitoring Quantifies Motion Behavior," *Design News* (Sep. 1986).

*Primary Examiner*—Francis Jaworski
*Attorney, Agent, or Firm*—Mason, Fenwick & Lawrence

[57] ABSTRACT

Apparatus for assessing posture, limb positions, and limb movements comprising a transmitter and a receiver for application to respective first and second skin positions, a microprocessor, and a biofeedback stimulus unit. The microprocessor measures the travel time of signals between the transmitter and the receiver, assesses the distance between the first and second skin positions based on the travel time of the signals between the transmitter and receiver, generates an actual posture parameter based upon the distance, compares the actual posture parameter with a predetermined target posture parameter stored in said microprocessor means, and generates a signal if the actual parameter is not equal to the target parameter. The biofeedback stimulus unit includes a patient-perceivable signal actuable in response to the signal generated by the microprocessor. The method comprises the steps of applying a transmitter and a receiver to first and second skin positions, respectively, which change their mutual distances during body movements due to the dilation or contraction of the areas of skin between the transmitter and receiver; measuring the travel time of signals from the transmitter to the receiver; and using the travel time measurements of the signals to calculate the distance changes.

14 Claims, 2 Drawing Sheets

METHOD AND APPARATUS FOR STIMULATION OF POSTURE

BACKGROUND OF THE INVENTION

1. Field of the Invention

The present invention is directed to the diagnosis of truncal musculature, and in particular, to a method of assessing posture and body movements using ultrasonic transducers to measure the running time of ultrasonic waves.

2. Related Art

For various medical applications, e.g., the diagnosis of truncal musculature, the method for the operant conditioning of subject's posture using biofeedback, the measurement of the joint angular position and the gait analysis, it is necessary to assess the posture and limb movements.

For these tasks devices of mechanic (U.S. 50 82 002, DD 251 075, EP 0154 102 A2), optic, electromagnetic (DE-OS 1 541 180, DE 2 715 106) and ultrasonic (WO 86/03 392 A1) bases are used.

All these known systems for the assessment of posture and limb positions as well as its movements have several significant drawbacks. For example, requiring a great apparatus display (optic systems), demanding sensors fixed in the room (ultrasonic and electromagnetic systems), allowing only a global evaluation of several posture parameters which are measured combined (cables extending longitudinally around the trunk to measure the spinal length), to be bulky and uncomfortable during application to the body, or easily to be damaged mechanically.

SUMMARY OF THE INVENTION

The invention has the object of providing a universal applicable method for measuring the posture and limb positions as well as its movements, operating precisely and proving to be cosmetically acceptable and considerably less physically restraining.

This object is achieved by the provision of a method for assessing the posture and limb positions using ultrasound or electro-magnetic fields/waves. The method operates indirectly, assessing the position of body parts by measuring the dilations or contractions of the skin, which occur during each body movement. The measurement is provided by an inter-distance measurement of a transmitter and a transducer, positioned side by side onto this skin area.

BRIEF DESCRIPTION OF THE DRAWINGS

An example of the invention is described with the aid of drawings.

DETAILED DESCRIPTION OF THE PREFERRED EMBODIMENT

Figure 1:
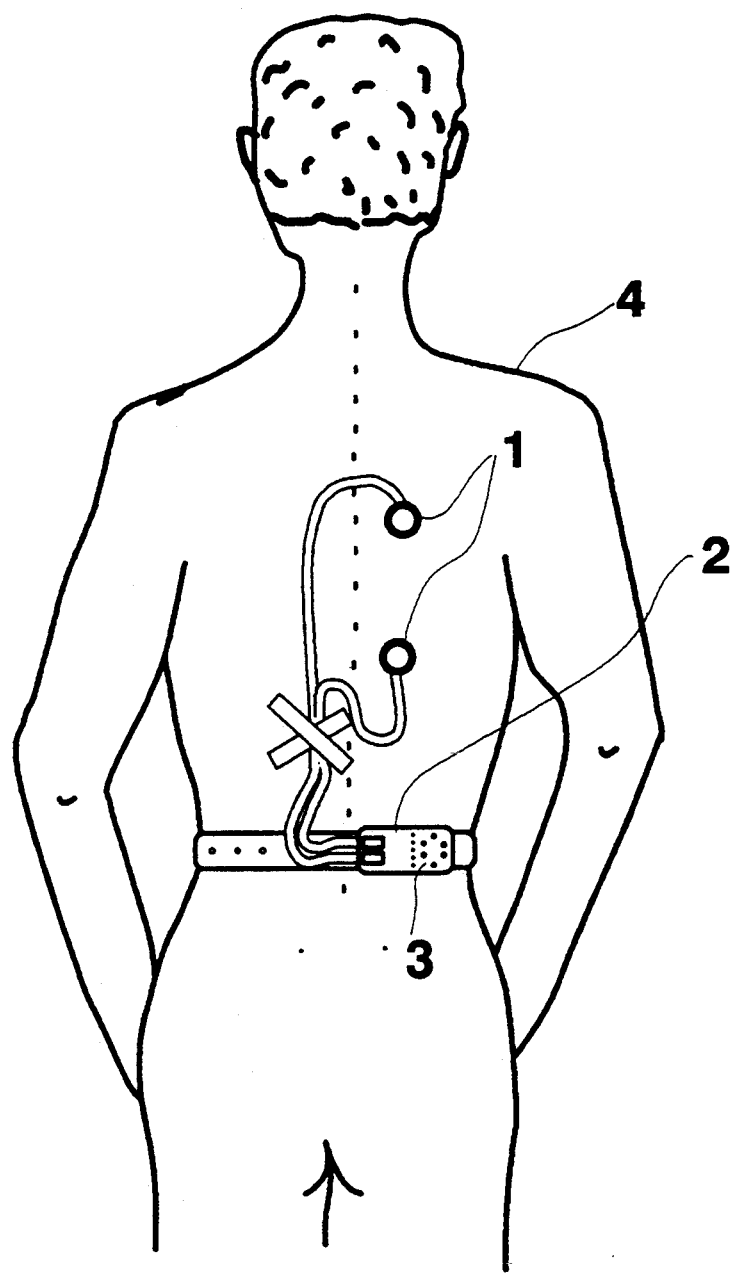
FIG. 1 shows the application of the system according the claims 1 or 5 for the operant conditioning of the subject's posture (curvature of spine).

The method for the assessment of posture and body movements, according to the invention, uses ultrasonic transducers 1 (transmitters and receivers) to measure the travel time of ultrasonic waves. The transducers 1 are applied at those positions on the skin 4 which change their mutual distance during body movements. Distance changes of the choosen skin positions are caused by dilatation/contraction of the skin 4 due to skin elasticity. For example, a knee flexion provides a skin tension about the patella, a knee extension causes a skin dilatation without skin folds. Position changes of limbs (e.g., approach the thigh to the leg during bending the knee) provides distance changes of fixed skin positions, too.

Due to precision of the ultrasonic technique, sufficient distance changes caused by body movements are already shown when transducer applications are provided with small mutual distances.

The application of ultrasonic transducers to the skin is favorably provided by adhesive substances or by means of tapes.

In a preferred embodiment of the invention, to assess the transducer distance, a path of travel for ultrasonic waves through superficial body layers (skin, fat, muscle) is preferred. To ensure the shortest ultrasound path of travel between the transducers 1 it is necessary to provide an ultrasound coupling by a flat angle to the skin 4 realized by an suitable transducer design.

In principle, the distance measurement is provided with short ultrasonic pulses. The first arriving pulse at the receiver is used for the travel time measurement. This principle is also operating, when the ultrasonic route between the transmitter and receiver is not exactly straight, is enclosing reflexions.

A sufficient divergent ultrasonic ray is provided, when the transducer cross-section will be chosen not to large in comparison to the ultrasonic wave length.

The choice of the ultrasonic wave length is conditioned by the transducer distance which is used for the measurement. Great transducer distances require partially greater wave lengths because of the ultrasonic attenuation in the body tissue.

In general the ultrasound running route via the air between the transducers 1 is suitable for the measurement, too. But the ultrasonic wave is very absorbed by clothes.

In particular, choosing the air route, the phase difference measurement between the transmitted and the received signals is preferred.

An important use of the method according to a preferred embodiment of the invention is the biofeedback of the posture for prophylaxis and therapy of spine curvature. In doing so, the distance between the transducers 1, according to the posture parameter of interest (e.g., shoulder sheet distance), is evaluated by an electronic unit 2 which compares the actual distance with a stored target distance, defined by the physician previously. If the criterion is not met, this may result in a negative reinforcement, such as unpleasant audio tone. The signaling to motivate the subject for correction of the spine is also possible by electric, mechanic, optic or thermal means.

Except that a rigid criterion of good posture can be used, a variable criterion depending on the patient's progress and tiring is possible for the triggering of the biofeedback signal.

The distance measurement provided by ultrasonic means according to the invention is also possible by known electro-magnetic means. In an alternate embodiment of the invention, electro-magnetic sensors (transmitter and receiver) are applied to the skin 4 as positions which change their mutual distances during body movements due to dilation or contraction of the area of skin between the sensors, and the dilation or contraction is assessed by the measurement of the distance between the sensors. The distance assessment is possible by measurement of the intensity of an electro-magnetic value, e.g., the intensity of a high-frequency field or of a magnetic field (the last by Hall-Generators).

Another possibility to assess a distance by electro-magnetic means is the measurement of the phase difference between the transmitted and the received signal. In doing so, the used electro-magnetic wave length has to be adapted according to the choosen transmitter-receiver-distance.

For a measurement system, to be based on the electro-magnetic technique, the same applying purposes exist as for the ultrasonic system.

Figure 2:
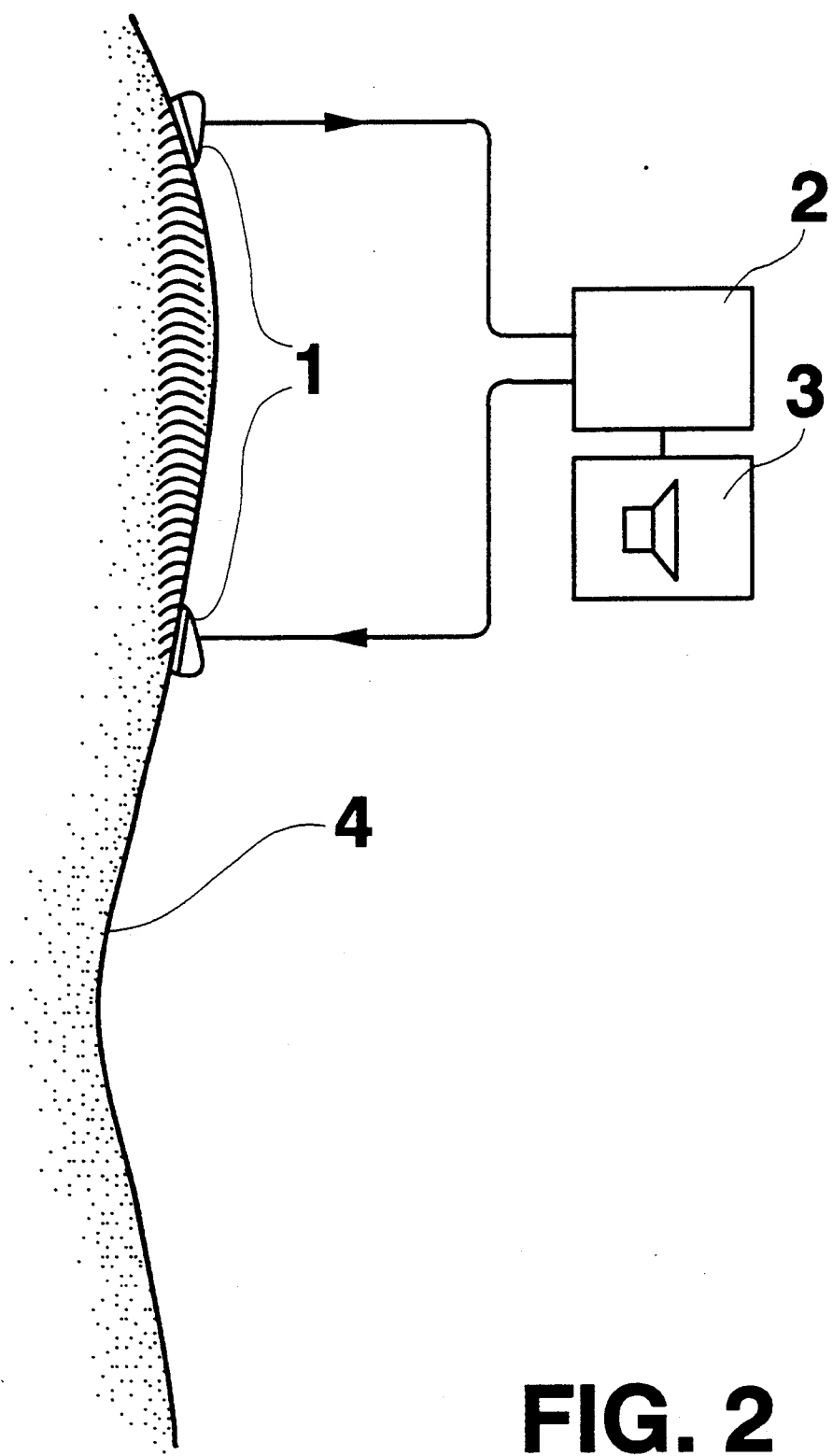
FIG. 2 shows a block diagram and partly an embodiment of the device according to the present invention as shown in FIG. 1, basing on ultrasonic technique.

FIG. 1 and 2 illustrate the use of the method, according to the invention for the therapy of kyphosis (curvature of the spine). The ultrasonic transmitters 1 are applied to the back vertically. The electronic unit 2 measures the travel time of the ultrasonic wave between the transducers 1 via the route through the body and computes the distance. If the distance is greater than the criterion (incorrect posture), defined by the physician, the signalizing unit 3 produces a bare tone likely to be heard only by the subject who wears the unit. This tone becomes louder when the poor posture is maintained for a time of about 15 sec. The louder tone may be heard by other people close to the subject.

Apparatus to effectuate the method according to the invention may comprise an electronic microprocessor unit to compare the actual parameter of posture with a previously defined and stored target parameter of good posture, and a biofeedback stimulus unit which stimulates the patient to reinforce his training. This apparatus can be battery powered and can be worn by the subject during the whole day.

A special use of the method, according to the invention, is aimed to assess the angle position as well as motion of the joints by applying ultrasonic transducers to the skin 4 in the area of the joints. In doing so, the right choice of the transducer positions is important because of the attenuation of ultrasound by bone. Moreover, the ultrasonic velocity in bone is different to the velocity in skin, fat and muscle.

For the measurement on the knee, the ultrasound running route medial to the patella and a transducer distance of a few centimeters are preferred.

I claim:

1. A method for indirectly assessing positions and movements of body parts of a subject for diagnostic purposes comprising the steps of:
   a) choosing a suitable skin area of a defined body part of the subject, the suitable skin area having elastic properties causing it to dilate or contract during position changes of the defined body part;
   b) applying a transmitter and a receiver to respective first and second skin positions of the suitable skin area which change their mutual distances during movements of the defined body part due to the dilatation or contraction of the skin between the transmitter and the receiver;
   c) using the transmitter to transmit a signal to the receiver;
   c) calculating the distance between the transmitter and the receiver by measuring a distance-dependant parameter of the signal transmitted from the transmitter to the receiver, the distance between the transmitter and the receiver representing the distance between the first and second skin positions; and
   d) comparing the distance between the transmitter and the receiver to a previously provided calibration to assess the position and the movement of the defined body part.

2. The method of claim 1, wherein in said step b), the first and second skin positions are in the area of the trunk, to assess posture and posture changes.

3. The method of claim 1, wherein in said step b), the first and second skin positions are in the area of a joint, to assess the motion of the joint and its angle.

4. The method of claim 1, wherein in said step b), the transmitter and the receiver are ultrasonic transducers, wherein in said step c), the signal is an ultrasonic wave, and wherein in said step d), the distance-dependant parameter is the travel time of the ultrasonic wave between the transducers, the travel time of the ultrasonic wave between the transducers being proportional to the distance between them.

5. The method of claim 4, wherein in said step b), the ultrasonic transducers are applied to provide a path of travel for the ultrasonic wave through the superficial layers of tissue.

6. The method of claim 4, wherein in said step b), the ultrasonic transducers are coupled to the skin at a substantially flat angle.

7. The method of claim 1, wherein in said step b), the transmitter and the receiver are coils, wherein in said step c), the signal is an electro-magnetic wave, and wherein in said step d), the distance-dependant parameter is the intensity of the electro-magnetic wave.

8. The method of claim 1, wherein in said step b), the transmitter and the receiver operate magnetically, wherein in said step c), the signal is a magnetic field, and wherein in said step d), the distance-dependant parameter is the intensity of the magnetic field.

9. The method of claim 1, wherein in said step c), the signal is an electro-magnetic wave, and wherein in said step d), the distance-dependant parameter is the phase difference between the transmitted and the received electro-magnetic wave.

10. Apparatus for assessing position and movement of a body part used for biofeedback in prophylaxis, therapy and rehabilitation, wherein the body part includes a suitable skin area which dilates or contracts during position changes of the body part due to the elastic properties of the skin in the area, said apparatus comprising:
   a transmitter for application to a first skin position in the suitable skin area;
   a receiver for application to a second skin position in the suitable skin area which changes its distance from the first skin position during movements of the body part due to the dilation or contraction of the skin area between the transmitter and the receiver;
   measuring and calculating means for measuring a distance-dependant parameter of signals travelling from the transmitter to the receiver and calculating the distance between the transmitter and the receiver based on the distance-dependant parameter, the distance between the transmitter and the receiver representing the distance between the first and second skin positions;
   microprocessor means for generating an actual position parameter of the body part based on the distance between the transmitter and the receiver calculated by said measuring and calculating means, comparing the actual position parameter with a predetermined target position parameter stored in said microprocessor means, and generating a signal if the actual parameter is not equal to the target parameter; and a biofeedback stimulus unit including a patient-perceivable signal actuable in response to the signal generated by said microprocessor means.

11. Apparatus of claim 10, wherein said transmitter and said receiver are ultrasonic transducers configured for coupling to the skin at a substantially flat angle, and wherein the distance-dependant parameter measured by said measuring means is the travel time of ultrasonic waves between said transducers.

12. Apparatus of claim 10, wherein said transmitter and said receiver are coils, and wherein the distance-dependant parameter measured by said measuring means is the intensity of an electro-magnetic wave generated by said coils.

13. Apparatus of claim 10, wherein said transmitter and said receiver are magnetic, and wherein the distance-dependant parameter measured by said measuring means is the intensity of a magnetic field generated by said transmitter and said receiver.

14. Apparatus of claim 10, wherein said transmitter includes means for emitting electro-magnetic waves and said receiver includes means for perceiving the electro-magnetic waves, and wherein the distance-dependant parameter measured by said measuring means is the phase difference between the transmitted and the received electro-magnetic waves.

* * * * *